United States Patent
Alessi et al.

(10) Patent No.: US 12,085,393 B2
(45) Date of Patent: Sep. 10, 2024

(54) USER CONTEXT AND ACTIVITY DETECTION DEVICE AND METHOD

(71) Applicant: STMICROELECTRONICS S.r.l., Agrate Brianza (IT)

(72) Inventors: Enrico Rosario Alessi, Catania (IT); Fabio Passaniti, Syracuse (IT)

(73) Assignee: STMICROELECTRONICS S.r.l., Agrate Brianza (IT)

( * ) Notice: Subject to any disclaimer, the term of this patent is extended or adjusted under 35 U.S.C. 154(b) by 4 days.

(21) Appl. No.: 17/198,160

(22) Filed: Mar. 10, 2021

(65) Prior Publication Data

US 2021/0285773 A1    Sep. 16, 2021

(30) Foreign Application Priority Data

Mar. 13, 2020    (IT) ................. 102020000005425

(51) Int. Cl.
*G01C 21/20* (2006.01)
*A61B 5/00* (2006.01)
(Continued)

(52) U.S. Cl.
CPC .......... *G01C 21/206* (2013.01); *A61B 5/1118* (2013.01); *A61B 5/681* (2013.01);
(Continued)

(58) Field of Classification Search
CPC ........ G01C 21/206; G01C 21/20; G01C 5/06; G01C 5/00; G01C 22/006; G01C 22/02;
(Continued)

(56) References Cited

U.S. PATENT DOCUMENTS 9,906,845 B2    2/2018  Alessi
10,324,214 B2   6/2019  Aponte Luis
(Continued)

FOREIGN PATENT DOCUMENTS

CN    1955978 A     5/2007
EP    2980609 A1    2/2016
(Continued)

OTHER PUBLICATIONS

Li M, Li P, Tian S, Tang K, Chen X. Estimation of Temporal Gait Parameters Using a Human Body Electrostatic Sensing-Based Method. Sensors (Basel). May 28, 2018;18(6):1737. doi: 10.3390/s18061737. PMID: 29843414; PMCID: PMC6022176. (Year: 2018).*
Kurita, Koichi & Morinaga, Syota. (2019). Detection Technique of Individual Characteristic Appearing in Walking Motion. IEEE Access. pp. 1-1. 10.1109/Access.2019.2943495. (Year: 2019).*
Ficker, "Charging by walking," *J. Phys. D: Appl. Phys.* 39:410-417, 2006.

*Primary Examiner* — Lisa M Caputo
*Assistant Examiner* — Eric Sebastian Von Wald
(74) *Attorney, Agent, or Firm* — Seed IP Law Group LLP

(57) ABSTRACT

A user context and/or activity detection device envisages a pressure sensor, configured to provide a pressure signal; an electrostatic-charge-variation sensor, configured to provide a charge-variation signal indicative of a variation of electrostatic charge associated with the user; and a processing unit, which is coupled to the pressure sensor and to the electrostatic-charge-variation sensor so as to receive the pressure signal and the charge-variation signal and is configured to jointly process the pressure signal and charge-variation signal for detecting changes in level or altitude.

35 Claims, 3 Drawing Sheets

(51) Int. Cl.
*A61B 5/11* (2006.01)
*G01C 5/06* (2006.01)

(52) U.S. Cl.
CPC ........ *G01C 5/06* (2013.01); *A61B 2560/0209* (2013.01); *A61B 2560/0257* (2013.01); *A61B 2562/0219* (2013.01)

(58) Field of Classification Search
CPC ......... A61B 5/1118; A61B 5/11; A61B 5/103; A61B 5/681; A61B 5/6802; A61B 5/6801; A61B 5/68; A61B 2560/0209; A61B 2560/0204; A61B 2560/0257; A61B 2560/0247; A61B 2560/0242; A61B 2562/0219; A61B 2562/02; G05B 2219/37325; G05B 23/0221; G16Y 40/00; G16Y 40/10; G16Y 40/20; G16Y 40/60; G01R 15/165; G10H 2220/321; G06F 1/163; G06Q 20/321
See application file for complete search history.

(56) References Cited

U.S. PATENT DOCUMENTS

| | | | | |
|---|---|---|---|---|
| 10,668,324 | B2* | 6/2020 | Case, Jr. | A63B 24/0075 |
| 10,694,325 | B2* | 6/2020 | Robertson | G01C 21/005 |
| 10,716,495 | B1* | 7/2020 | Romrell | A61B 5/112 |
| 11,045,116 | B1* | 6/2021 | Martin | A61B 5/112 |
| 2003/0136191 | A1 | 7/2003 | Tsuji | |
| 2014/0232516 | A1 | 8/2014 | Stivoric et al. | |
| 2016/0258758 | A1* | 9/2016 | Houston | G01D 5/145 |
| 2016/0342781 | A1 | 11/2016 | Jeon | |
| 2019/0101387 | A1* | 4/2019 | Jackson | G01C 5/00 |
| 2019/0383606 | A1* | 12/2019 | Karvounis | G01C 21/206 |
| 2020/0197783 | A1* | 6/2020 | Iida | G06F 3/14 |
| 2020/0229736 | A1* | 7/2020 | Saporito | G06F 3/011 |
| 2021/0267486 | A1* | 9/2021 | Rosato | A61B 5/7455 |

FOREIGN PATENT DOCUMENTS

| | | |
|---|---|---|
| KR | 20110061750 A | 6/2011 |
| KR | 20130138481 A | 12/2013 |

* cited by examiner

USER CONTEXT AND ACTIVITY DETECTION DEVICE AND METHOD

BACKGROUND

Technical Field

The present solution relates to a user context and activity detection device and method, in particular for detecting level (or in general altitude) changes, more in particular floor changes in a building associated with climbing or descending staircases.

Description of the Related Art

Mobile electronic apparatuses (such as smartphones, tablets, phablets, and the like) and wearable electronic apparatuses (such as bracelets, smartwatches, earpieces, and the like) are provided with detection modules integrating a number of sensors (for example, inertial movement sensors, pressure sensors, temperature sensors, etc.). The aforesaid detection modules, in addition to providing information designed for managing operation of the electronic devices, for example for implementing corresponding user interfaces, may provide information useful for locating the user, for the purpose, for example, of enabling provision of messages, services or alerts linked to the context (so-called context-based or context-aware), and moreover information linked to the physical activity of the user, for example in order to monitor the consumption of calories or a distance covered.

In this regard, for example when the user is inside a building, it is useful to have the possibility of detecting changes in level (or in general altitude), in particular floor changes associated with a user going up or downstairs, so as to propose appropriate context-based activities, messages, services, or functions; and moreover so as to accurately monitor the physical activity of the user inside the building.

For the aforesaid detection modules of mobile or wearable electronic apparatuses a low energy consumption, a low latency (a low response delay) and a high accuracy are generally desired.

In order to detect the aforesaid level changes, use of detection modules based on a pressure or barometric sensor is employed, in which a corresponding processing unit is configured to monitor, via appropriate algorithms, the variations of the pressure signal and to identify a change in level as a function of the variations of the pressure signal.

For example, U.S. Pat. No. 9,906,845 B2 filed in the name of the present Applicant, envisages use of a state machine appropriately configured to process the aforesaid pressure signal.

Other solutions envisage the use, in addition to the pressure or barometric sensors, of movement sensors, in particular accelerometric sensors.

BRIEF SUMMARY

The aforesaid solutions are not, however, altogether satisfactory, in particular due to: a high computational cost both in the case of single-technology solutions (based on a single pressure sensor) and of dual-technology solutions (based on a pressure sensor and a movement sensor); possible detection errors (the so-called false positives or false negatives) due to noise and disturbance factors, for example constituted by the movement of the user's limbs (in the case of wearable electronic apparatuses, such as bracelets or smartwatches); a high latency, due to the need to wait for sufficient wait times in order to prevent the aforesaid false detections; and a high demand for buffer memory, for temporary storage of data during the aforesaid wait times.

Furthermore, generally, dual-technology solutions have a high occupation of area and a high-energy consumption, given that the pressure and movement sensors are typically made in two distinct and separate chips (each integrated in a respective package).

The need is consequently felt to overcome the drawbacks of the prior art by providing a user context and activity detection device and method, in particular for detecting changes in level, more in particular changes of floor associated with climbing or descending staircases, being inexpensive yet reliable and having a low computational load.

In an embodiment, a device comprises: a pressure sensor, configured to provide a pressure signal; an electrostatic-charge-variation sensor, configured to provide a charge-variation signal indicative of a variation of electrostatic charge; and circuitry, coupled to the pressure sensor and to the electrostatic-charge-variation sensor and configured to detect changes in level based on the pressure signal and on the charge-variation signal. In an embodiment, the circuitry is configured to: process a pressure gradient over time, associated with a variation of the pressure signal, to detect a first indication of change in level; process a variation of the charge-variation signal over time to detect a second indication of change in level; and determine an occurrence of a change in level in response to detection of the first and second indications during a threshold time interval. In an embodiment, the change in level is associated with a user going one step upstairs or one step downstairs, the first indication is detected in response to the pressure gradient exceeding, in absolute value, a first pressure threshold, indicative of the variation of the pressure signal associated with going one step up or one step down, and the second indication is detected in response to detection of a variation of the charge-variation signal associated with the user going one step up or one step down. In an embodiment, the circuitry is configured to detect a variation of the charge-variation signal associated with the user going one step up or one step down by extraction and analysis of features of the charge-variation signal. In an embodiment, the analysis of features of the charge-variation signal includes: detecting peaks of amplitude of the charge-variation signal that exceed a threshold; detecting patterns of the charge-variation signal; or combinations thereof. In an embodiment, the circuitry is configured to implement a counting of the steps up or down associated with the user based on the pressure signal and the charge-variation signal. In an embodiment, the circuitry is configured to: set a baseline value of the pressure signal during a stationary condition; and at the end of the user climbing or descending a staircase: determine a difference between a current value and the baseline value of the pressure signal; determine a change of floor based on a comparison between the difference and a second pressure threshold, indicative of the variation of the pressure signal associated with the user going one floor up or one floor down; and incrementing a count of floors ascended or descended by the user based on the determining of a change of floor. In an embodiment, wherein the electrostatic-charge-variation sensor comprises: at least one electrode; an amplifier having an input coupled to the at least one electrode; and an analog-to-digital converter coupled to an output of the amplifier for supplying the charge-variation signal. In an embodiment, the device comprises an integrated circuit including the circuitry, the pressure sensor, and the electrostatic-charge-variation sensor.

In an embodiment, a system comprises: an application processor; sensing circuitry coupled to the application processor, the sensing circuitry including: a pressure sensor, which, in operation, generates a pressure signal; a charge sensor, which, in operation, generates a charge signal; and control circuitry, coupled to the pressure sensor and to the charge sensor, wherein the control circuitry, in operation, detects changes in level based on the pressure signal and on the charge signal. In an embodiment, the control circuitry, in operation, detects a first indication of a change in level based on the pressure signal; detects a second indication of a change in level based on the charge signal; and determines an occurrence of a change in level in response to detection of the first and second indications during a threshold time interval. In an embodiment, control circuitry, in operation: detects the first indication based on a comparison of a pressure gradient to a first pressure gradient threshold. In an embodiment, the first pressure gradient threshold is indicative of a pressure gradient associated with going up or going down a stair. In an embodiment, the control circuitry, in operation: detects the second indication based on features extracted from the charge signal. In an embodiment, the control circuitry, in operation: detects the second indication based on: comparisons of peaks of amplitude of the charge signal to a charge-signal threshold; patterns detected in the charge signal; or combinations thereof. In an embodiment, the control circuitry, in operation, counts changes in step-level associated with a user based on the determined occurrences of changes in level. In an embodiment, the control circuitry, in operation: sets a baseline value of the pressure signal in response to detecting a stationary condition; and in response to an indication a user has climbed or descended a staircase: determines a difference between a current value and the baseline value of the pressure signal; determines a change of floor based on a comparison between the difference and a second pressure threshold, indicative of the variation of the pressure signal associated with the user going one floor up or one floor down; and increments a count of floors ascended or descended by the user based on the determining of a change of floor.

In an embodiment, a method comprises: generating, using a pressure sensor of a device, a pressure signal; generating, using a charge sensor of the device, a charge signal; and detecting changes in user-level based on the pressure signal and on the charge signal. In an embodiment, the method comprises: detecting a first indication of a change in user-level based on the pressure signal; detecting a second indication of a change in user-level based on the charge signal; and determining an occurrence of a change in user-level in response to detection of the first and second indications during a threshold time interval. In an embodiment, the method comprises: detecting the first indication based on a comparison of a pressure gradient to a first pressure gradient threshold. In an embodiment, the first pressure gradient threshold is indicative of a pressure gradient associated with going up or going down a stair. In an embodiment, the method comprises: detecting the second indication based on features extracted from the charge signal. In an embodiment, the method comprises detecting the second indication based on: comparisons of peaks of amplitude of the charge signal to a charge-signal threshold; patterns detected in the charge signal; or combinations thereof. In an embodiment, the method comprises: counting changes in step-level associated with a user based on the occurrences of changes in user-level. In an embodiment, the method comprises: setting a baseline value of the pressure signal in response to detecting a stationary condition; and in response to an indication that a user has climbed or descended a staircase: determining a difference between a current value and the baseline value of the pressure signal; determining a change of floor based on a comparison between the difference and a second pressure threshold, indicative of the variation of the pressure signal associated with the user going one floor up or one floor down; and incrementing a count of floors ascended or descended by the user based on the determining of a change of floor.

In an embodiment, a non-transitory computer-readable medium's contents that configure an electronic device to perform a method, the method comprising: generating, using a pressure sensor of the electronic device, a pressure signal; generating, using a charge sensor of the electronic device, a charge signal; and detecting changes in user-level based on the pressure signal and on the charge signal. In an embodiment, the method comprises: detecting a first indication of a change in user-level based on the pressure signal; detecting a second indication of a change in user-level based on the charge signal; and determining an occurrence of a change in user-level in response to detection of the first and second indications during a threshold time interval. In an embodiment, the method comprises: counting changes in step-level associated with a user based on the occurrences of changes in user-level. In an embodiment, the contents comprise instructions executed by sensor-signal processing circuitry of the electronic device.

According to the present solution, a detection device and method are provided.

BRIEF DESCRIPTION OF THE SEVERAL VIEWS OF THE DRAWINGS

For a better understanding of the disclosure, embodiments thereof are now described, purely by way of non-limiting example and with reference to the attached drawings, wherein.

DETAILED DESCRIPTION

As will be described in detail hereinafter, one aspect of the present solution envisages, for user context and activity detection, in particular for detecting changes in level or altitude, more in particular changes of floor in a building associated with climbing or descending staircases, a detection device based on the joint use, in combination, of a pressure sensor (or barometric sensor) and of an electrostatic-charge-variation sensor.

The electrical charge is a fundamental component of nature. The electrical charge of an electrostatically charged body can be easily transferred to another body, in conditions of direct contact or remotely. When charge is transferred between two electrically insulated objects, a static charge is generated so that the object with an excess of electrons is negatively charged, and the object with a deficit of electrons is positively charged. The displacement of charges is of a different nature according to whether the object is a conductive object or a dielectric. In a conductor, the electrons are distributed throughout the material and are free to move, based on the influence of external electrical fields. In a dielectric, there are no electrons free to move but electric dipoles, with random directions in space (therefore with zero resulting net charge), which, however, can be directed or deformed by applying an external electrical field, thus generating an orderly distribution of charges and therefore a polarization. Charge may in any case be mobile according to the properties of the material and other environmental factors.

In an embodiment of the present solution, the electrostatic-charge-variation sensor of the detection device is configured to detect, by means of a capacitive detection, the variations of electrical field that occur during the movements of the user, as a result of the transfer of charges from the user's body to the ground as the user performs steps, in particular, when climbing or descending the steps of a staircase.

Figure 1:
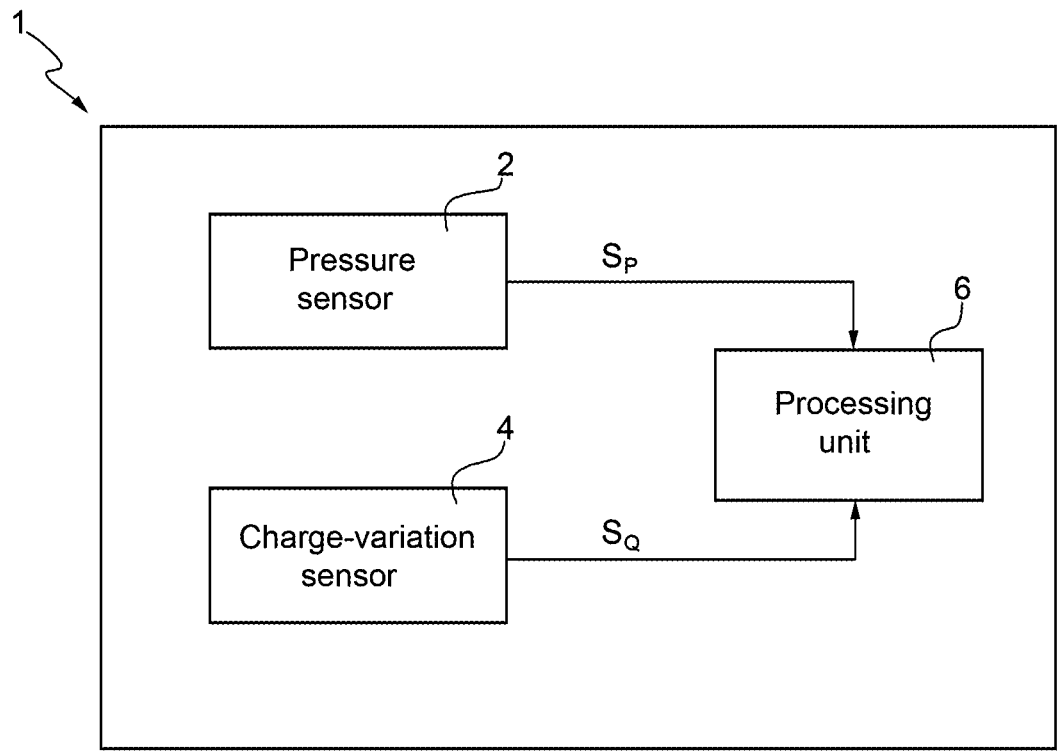
FIG. 1 is a schematic illustration of a detection device, according to an embodiment of the present solution.

FIG. 1 is a schematic illustration of a detection device 1 according to an embodiment of the present solution, which comprises:

- a pressure sensor 2, for example an integrated sensor made of semiconductor material, with MEMS (Micro-Electro-Mechanical System) technology, of a per se known type (not described in detail herein) and designed to provide a pressure signal $S_P$ indicative of a pressure or pressure change as a function of the pressure (or barometric level) acting on the detection device 1;
- an electrostatic-charge-variation sensor 4, an embodiment of which will be described in detail hereinafter, designed to provide a charge-variation signal $S_Q$ indicative of a variation of electrostatic charge associated with the user; and
- a processing unit 6, which is coupled to the pressure sensor 2 and to the electrostatic-charge-variation sensor 4 in order to receive the pressure signal $S_P$ and the charge-variation signal $S_Q$ and is configured to jointly process the aforesaid pressure signal $S_P$ and charge-variation signal $S_Q$ to detect changes in level, more in particular changes of floor associated with the user climbing or descending the steps of a staircase.

The processing unit 6 comprises, for example, a microcontroller, or an MLC (Machine-Learning Core) processor residing in an ASIC (Application-Specific Integrated Circuit) coupled to the pressure sensor 2 and to the electrostatic-charge-variation sensor 4 for processing of the corresponding pressure signals $S_P$ and the charge-variation signal $S_Q$; the aforesaid pressure sensor 2, electrostatic-charge-variation sensor 4, and processing unit 6 may be provided within a same package provided with appropriate elements for electrical connection to the outside environment, for example for connection to a host electronic apparatus, for instance a mobile or wearable apparatus.

Figure 2:
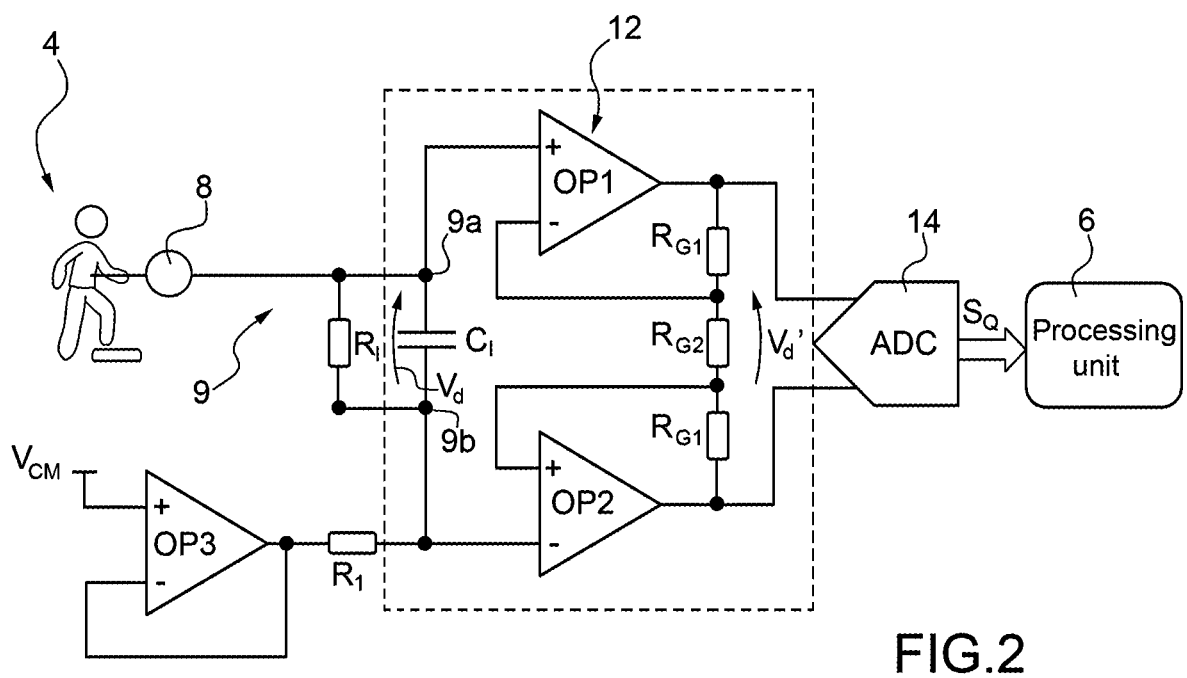
FIG. 2 illustrates a possible embodiment of an electrostatic-charge-variation sensor of the detection device of FIG. 1.

FIG. 2 illustrates an embodiment, provided by way of non-limiting example, of the electrostatic-charge-variation sensor 4, which comprises at least one input electrode 8, which is designed to be arranged in direct contact with, or in the proximity of, a portion of a user's body.

For instance, in the case where the detection device 1 is integrated in a wearable device, such as a smartwatch, the input electrode 8 can be arranged on the outside of a corresponding casing so as to be in direct contact with the user's wrist. It is emphasized, however, that in general direct contact with the conductive material of the electrode is not required. For example, a separation by means of dielectric material, with a thickness in the order of millimetres, is also possibly envisaged.

The input electrode 8 forms part of a differential input 9 of an instrumentation amplifier 12, being coupled to a corresponding first input terminal 9a.

An input capacitor $C_I$ and an input resistor $R_I$ are connected in parallel to one another between the first input terminal 9a and a second input terminal 9b of the differential input 9.

During operation, an input voltage $V_d$ across the input capacitor $C_I$ varies due to the process of electrical charging/discharging through the user's body, in particular due to contact with the ground, more in particular as a result of the user going up or down the steps of a staircase. After a transient (the duration of which is given by the $R_I \cdot C_I$ constant defined by the parallel between the capacitor $C_I$ and the resistor $R_I$), the input voltage $V_d$ returns to its steady state value.

The instrumentation amplifier 12 is basically constituted by two operational amplifiers OP1 and OP2, which have non-inverting input terminals connected, respectively, to the first and second input terminals 9a, 9b and inverting terminals connected together via a gain resistor $R_{G2}$.

A biasing stage (buffer) OP3 biases the instrumentation amplifier 12 to a common-mode voltage $V_{CM}$, through a resistor $R_1$ coupled to the second input terminal 9b.

The output terminals of the operational amplifiers OP1 and OP2 are connected to the respective inverting input terminals via a respective gain resistor $R_{G1}$; an output voltage $V_d'$ is present between the output terminals.

The gain of the instrumentation amplifier 12 is equal to $(1+2 \cdot R_1/R_2)$; consequently, the aforesaid output voltage $V_d'$ is equal to: $V_d \cdot (1+2 \cdot R_1/R_2)$.

The components of the instrumentation amplifier 12 may be chosen so that the same instrumentation amplifier 12 has a low noise and a high impedance (for example, of the order of $10^9 \Omega$) in its operating bandwidth (for example, comprised between 0 and 500 Hz).

The aforesaid output voltage $V_d'$ is provided at the input of an analog-to-digital converter (ADC) 14, which provides at its output the aforesaid charge-variation signal $S_Q$ for the processing unit 6. The charge-variation signal $S_Q$ is, for example, a high-resolution digital signal (with 16 bits or 24 bits).

According to a different embodiment, if an analog-to-digital converter 14 is available with appropriate characteristics (e.g., differential input, high input impedance, high resolution, dynamic range optimized for the quantities to be measured, low noise), the instrumentation amplifier 12 can be omitted, in this case the input voltage $V_d$ being directly supplied to the input of the analog-to-digital converter 14.

In a way not illustrated, the charge-variation signal $S_Q$ can be provided to a first input of a multiplexer block, which can moreover receive the aforesaid pressure signal $S_P$ on at least one further input (and possibly additional detection signals, for example a temperature signal, on further inputs). The output of the multiplexer block is in this case coupled to an input of the processing unit 6 so as to provide, sequentially in time, the aforesaid charge-variation $S_Q$ and pressure $S_P$ signals (and possibly further detection signals) for joint processing by the processing unit 6.

Figure 3:
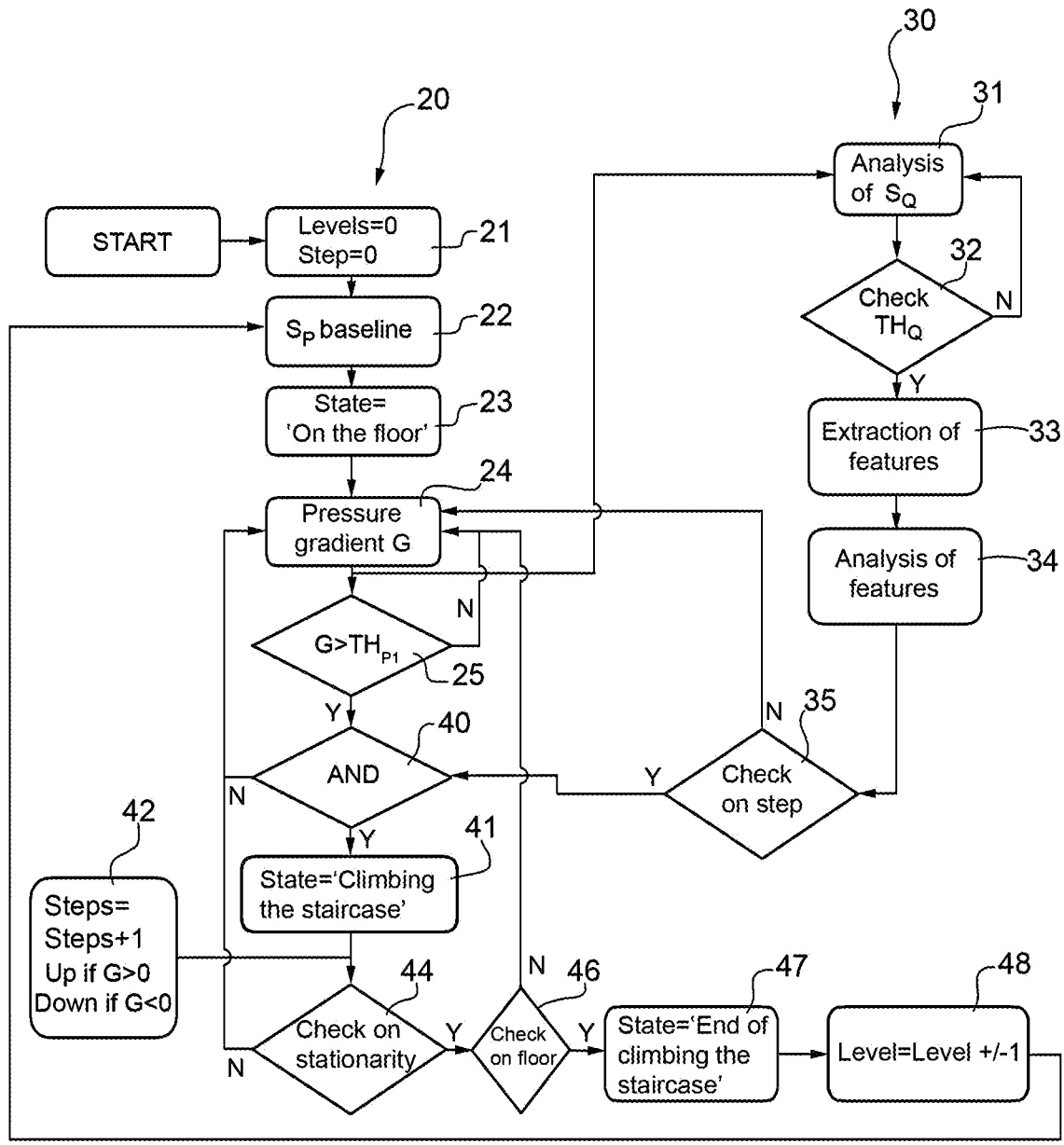
FIG. 3 illustrates a flowchart of a method implemented by the detection device of FIG. 1, according to an embodiment of the present solution.

FIG. 3 illustrates, by means of a flowchart, the operations of joint processing of the charge-variation and pressure signals $S_Q$, $S_P$ carried out by the processing unit 6 according to a possible embodiment of the present solution.

In an embodiment, the processing unit 6 is configured to execute in parallel (in a substantially simultaneous manner) two distinct processing branches, one for processing of the charge-variation signal $S_Q$ and the other for processing of the pressure signal $S_P$ (in the embodiment described, both signals being of a digital type), and to detect changes in level, more in particular changes of floor associated with the user climbing or descending a staircase, based, in a joint manner, on the results of the aforesaid processing branches.

In detail, the first processing branch, designated by 20, envisages in an initial step (for example, upon entry of the user into a building or similar closed environment), at block 21, initialization to zero of a variable "Level", which represents the count of floors or levels ascended or descended by the user, and of a variable "Steps", which represents the count of steps made by the user during the activity of climbing or descending the staircase.

In particular, "Level=0" represents the initial starting level; "Level=−1" indicates that the user is on a floor directly below the starting level; "Level=+1" indicates that the user is on a floor directly above the starting level; and so forth.

Moreover, in block 22, a baseline level of the pressure signal $S_P$, determined at the starting level ("Level=0") is set; and, in block 23, the value of a state variable "State" is set as "On the floor" (this state variable can moreover assume, as will be seen hereinafter, the values "Climbing the staircase" and "End of climbing the staircase", according to the activity of the user).

In block 24, the value of a pressure gradient G is then calculated, continuously in time, within a cyclic loop, representing the difference between a current value (in particular, a sample) and a previous value of the pressure signal $S_P$.

As shown in block 25, the above pressure gradient G is compared, in absolute value, with a first pressure threshold $Th_{P1}$, of a determined value which may be a pre-set value, indicative of the variation of the pressure signal associated with going one step up or down (the value of this first pressure threshold $Th_{P1}$ can be determined beforehand or in an initial characterization phase).

If the pressure gradient G is, in absolute value, below the first pressure threshold $Th_{P1}$, processing returns to block 24 to calculate a new value of the pressure gradient (considering the next value of the pressure signal $S_P$).

If, instead, the pressure gradient G is, in absolute value, equal to or higher than the first pressure threshold $Th_{P1}$, the first processing branch provides a first indication of the fact that the user is climbing or descending a staircase and in particular has gone one step up or down.

In parallel, the second processing branch, designated by 30, envisages, as illustrated in block 31, continuously in time and within a respective cyclic loop, processing of the charge-variation signal $S_Q$ (possibly preliminarily subjected to appropriate filtering actions).

In the embodiment illustrated, by way of example, the aforesaid block 31 is executed subsequently to block 24, described previously.

In particular, at block 32, a preliminary check of the charge-variation signal $S_Q$ is first made in order to identify a significant variation thereof with respect to a reference (or baseline) value.

In a possible embodiment, the aforesaid preliminary check may be made via a comparison of the charge-variation signal $S_Q$ with a charge threshold $Th_Q$. The charge threshold $Th_Q$ may be fixed and may be pre-set, or, alternatively, may be adaptive, for example, variable as a function of the pattern of the charge-variation signal $S_Q$. The calculation of the charge threshold $Th_Q$ of an adaptive type can be carried out by exploiting techniques known in the art; for example, it is possible to use sliding windows or overlapping windows, or again other techniques for real-time adaptive-threshold calculation.

In a possible embodiment, the charge threshold $Th_Q$ can be chosen as the average of the charge-variation signal $S_Q$ (in the time window considered) plus a multiple of the standard deviation of the same charge-variation signal $S_Q$ (in the window considered), as follows:

$$Th_Q = \text{mean}(S_Q) + n \cdot \text{stddev}(S_Q),$$

where "n" is chosen in the range between 2 and 6, for example 4 (where "mean" represents the operation of arithmetical mean, and "stddev" represents the operation of standard deviation). The time window may be chosen of an appropriate value. This value depends on the type of application; the Applicant has found that values compatible with a processing on a microcontroller (taking into consideration the buffers, the memory used and the computational resources), the time window can, for example, range from 2 to 10 seconds.

If the preliminary check on the charge-variation signal $S_Q$ does not lead to identification of a significant variation, processing returns to block 31, for a new processing cycle of the same charge-variation signal $S_Q$.

If, instead, the aforesaid significant variation of the charge-variation signal $S_Q$ is identified, a further and more in-depth analysis of the charge-variation signal $S_Q$ is carried out in order to verify the presence of features that are indicative of a step made by the user, in particular whether the same user has gone one step up or one step down.

The above further analysis may envisage, in a simpler (and less burdensome from the computational standpoint) embodiment, the identification of (positive and/or negative) peaks in the pattern of the charge-variation signal $S_Q$ with respect to a reference value, due to the transfer of electrostatic charges to the ground.

As will also be pointed out hereinafter, the present Applicant has in fact verified the possibility of identifying peaks in the charge-variation signal $S_Q$ at each step, in particular in the case of the user climbing or descending a staircase, as a result of the aforesaid transfer of charges from the user's body to ground.

In a different embodiment, illustrated in the aforesaid FIG. 3, which is more burdensome from the computational standpoint but ensures an improved accuracy in the detection of the steps, the aforesaid further analysis of the charge-variation signal $S_Q$ can be carried out by means of a dual step of extraction of significant features of the charge-variation signal $S_Q$ (block 33) and of analysis of the extracted features (block 34).

The aforesaid significant features characterize the pattern of the charge-variation signal $S_Q$, for example of a corresponding envelope, and can be identified and detected by means of processing of the same charge-variation signal $S_Q$. Advantageously, to carry out the aforesaid operations of extraction and analysis of features, it is possible to use machine-learning artificial-intelligence algorithms (models) that are appropriately trained, for example by means of neural networks, SVMs, Bayesian networks, etc.

According to the further analysis, a check is made on the presence in the charge-variation signal $S_Q$ of features indicative of the step made the user (in particular, corresponding to a step of the staircase), block 35.

If no such feature is present, processing envisages a subsequent processing cycle of the same charge-variation signal $S_Q$ (in the example, return to the aforesaid block 24).

Otherwise, a second indication is instead provided of the fact that the user is climbing or descending a staircase and in particular that the same user has gone one step up or down.

In particular, in block 40, the processing envisages verifying the simultaneous presence, substantially at a same instant or in a same time interval or within a threshold period of time, of the aforesaid first and second indications, in order to validate (in the case of positive outcome from verification of the aforesaid simultaneous presence) detection of the fact that the user has gone one step up or one step down. In other words, in block 40, a (temporal) AND operation is carried out between the first and second indications.

It is pointed out that a certain delay (for example, of the order of a few tens of milliseconds) between the two detections of the first and second indications is in any case acceptable given that it falls within the normal delay of generation, acquisition and processing of two signals (by means of operations carried out with procedures that are different from one another).

In case where the simultaneous presence of the first and second indications is effectively verified, control passes from block 40 to block 41, where the state variable "State" is set to the value "Climbing the staircase".

Moreover, block 42, the variable "Steps" is incremented (Steps=Steps+1).

In a possible embodiment, two distinct counters can be used for counting steps up or down. Distinction between a step up and a step down may be based only on the pressure gradient G, according to whether it is positive or negative. Alternatively, advantageously, a joint evaluation of the pressure gradient G and of further features of the charge-variation signal $S_Q$ can be carried out. As will be highlighted hereinafter, in fact, it is possible to distinguish a step up from a step down by the presence of different features in the pattern of the charge-variation signal $S_Q$.

As highlighted in block 44, the parallel processing of the pressure signal $S_p$ and of the charge-variation signal $S_Q$ then continues until a check made on the pressure signal $S_P$ indicates stationarity thereof.

In one embodiment, the stationarity check consists, for example, in verifying whether the pressure signal $S_P$ has significant variations (with respect to a given threshold) within a given time interval.

After verifying that the pressure signal $S_P$ is stationary, a further check is made to verify whether the user has actually gone one floor up or one floor down (instead of, for example, retracing his steps back to the starting level).

For this purpose, block 46, the pressure difference is calculated between the current value of the pressure signal $S_P$ and the baseline level of the same pressure signal $S_P$ (set previously) and a check is made to verify whether this difference is greater, in absolute value, than a second pressure threshold $Th_{P2}$, of a determined value which may be a pre-set value, indicative of the variation of the pressure signal associated with going one floor up or one floor down (the value of the second pressure threshold $Th_{P2}$ can be determined beforehand or in an initial characterization step).

If the aforesaid pressure difference is lower, in absolute value, than the second pressure threshold $Th_{P2}$, the processing returns to the aforesaid block 24, for a new cyclic processing of the pressure gradient G and, in parallel, of the charge-variation signal $S_Q$.

If, instead, the aforesaid pressure difference is, in absolute value, greater than or equal to the second pressure threshold $Th_{P2}$, the state variable "State" is set at the value "End of climbing the staircase", block 47; moreover, block 48, the variable "Level" is incremented (or decremented, according to the sign of the pressure difference), Level=Level±1.

Processing then returns to block 22, where the baseline level of the pressure signal $S_P$ is set to the current value of the pressure signal $S_P$, after which the processing continues as described previously, in a cyclic way.

Figure 4:
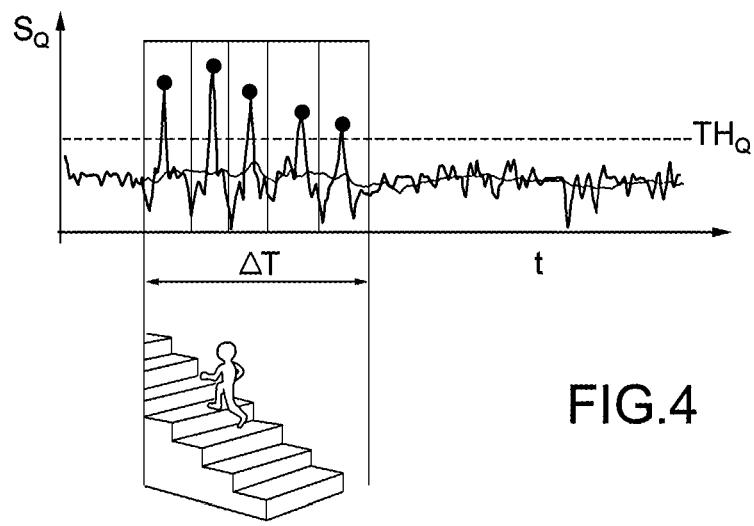
FIGS. 4 and 5 show plots of an electrostatic-charge-variation signal detected while a user is going upstairs/downstairs.

FIG. 4 shows the pattern of the charge-variation signal $S_Q$ during the activity of the user climbing the staircase, which occurs, as illustrated schematically, in a time interval identified by ΔT. In particular, it is evident that, for each step up a peak occurs (indicated by a dot), and moreover a characteristic pattern (indicated by a rectangular box) in the charge-variation signal $S_Q$, which can therefore be identified via processing of the signal by the processing unit 6.

Indicated once again in FIG. 4 is the charge threshold $Th_Q$, which is, for example, calculated in an adaptive manner with respect to the pattern of the charge-variation signal $S_Q$, in particular with respect to a mean value (the pattern of which is traced with a dashed line) of the same charge-variation signal $S_Q$. The peaks therefore refer in this case to the aforesaid charge threshold $Th_Q$.

It is moreover evident that, outside the aforesaid time interval ΔT, for example in conditions where the user is walking normally, the charge-variation signal $S_Q$ has considerably different features, and in particular an amplitude below the charge threshold $Th_Q$.

Figure 5:
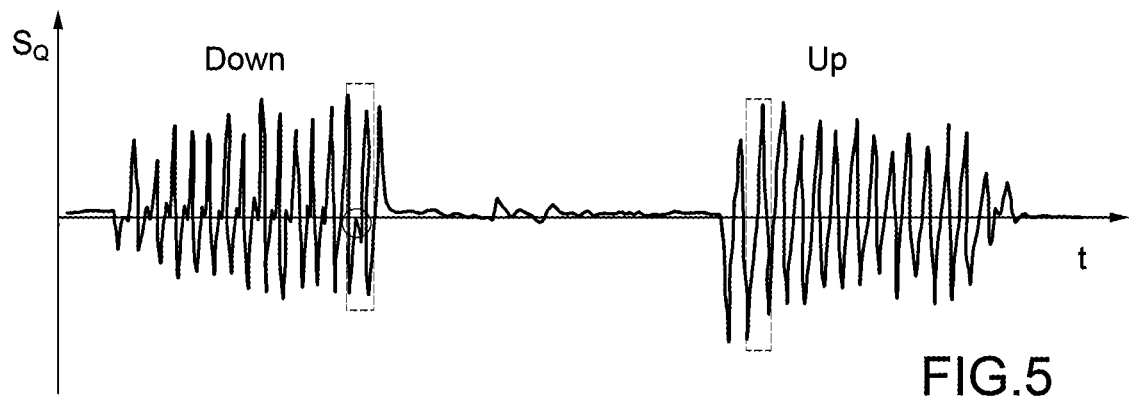

FIG. 5 again shows the pattern of the charge-variation signal $S_Q$, this time both during the activity of the user going downstairs (time interval identified by "DOWN") and during the activity of the user going upstairs (time interval identified by "UP"). It is evident how the characteristic pattern of the signal at each step up is sensibly different from the characteristic pattern of the signal at each step down, thus enabling identification, as discussed previously, of the steps up and the steps down and corresponding distinct counting. In particular, as indicated in the boxed portion (for a single step, provided by way of example), during a step down a natural movement of opposition to the force of gravity, or braking, is made by the user, which determines a characteristic pattern in the charge-variation signal $S_Q$ that is not, instead, present when the user is going upstairs.

Figure 6:
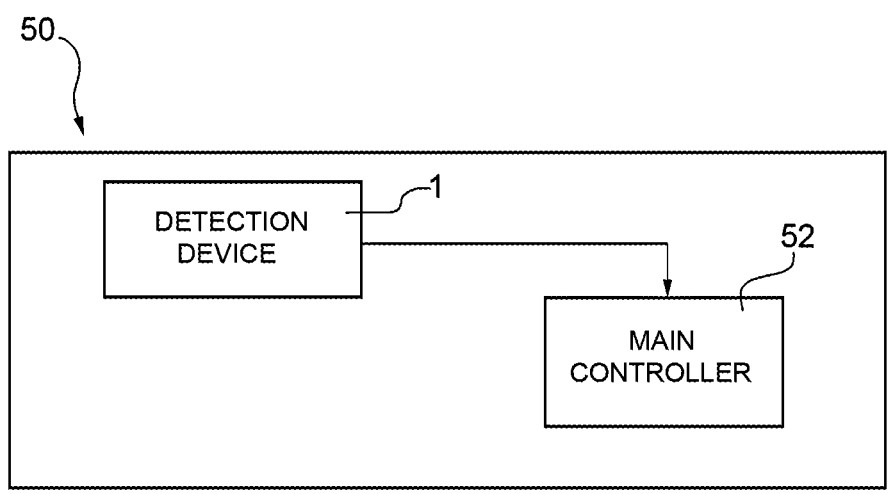
FIG. 6 is a general block diagram of an electronic apparatus in which the detection device of FIG. 1 can be used.

FIG. 6 is a schematic illustration of an electronic apparatus 50 that includes the detection device 1 described previously; for example, the electronic apparatus 50 is a mobile electronic apparatus (such as a smartphone, tablet, phablet or the like) or a wearable apparatus (such as a bracelet, a smartwatch, an earpiece or the like).

The electronic apparatus 50 comprises a main controller 52 (a microcontroller, a microprocessor or similar digital processing unit), coupled to the processing unit 6 of the detection device 1, in order to receive information regarding the changes of floor or the changes in level, more in particular associated with the user climbing or descending a staircase.

In the embodiment described previously, the main controller 52 receives, for example from the processing unit 6 of the detection device 1, the values detected for the Level, Steps, and State variables in order to provide, in a per se known manner and not described in detail herein, context-based messages, services or alerts and moreover obtain information linked to the physical activity of the user, for example in order to monitor the consumption of calories or a distance covered.

The advantages achieved by the present solution emerge clearly from the foregoing description.

In any case, it is once again highlighted that in the detection device 1, the monitoring of charge variation enables reinforcement of the information associated with only the pressure detection.

In particular, the detection device 1 enables optimization of the performance (in particular, reducing the number of false detections, false positives and false negatives), with an optimised energy consumption and a reduced occupation of space (in particular, integrating in a single package both detection technologies, pressure detection and charge-variation detection).

As described previously, there is the advantageous possibility of obtaining from the charge-variation signal $S_Q$ also information regarding climbing or descending the staircase, which can be used jointly with the information on the pressure gradient G to increase the accuracy of detection.

In this regard, it is pointed out that known step-counting solutions based on accelerometric sensors are not, instead, able to discriminate between the steps made when going upstairs and downstairs.

Furthermore, the present solution has a reduced latency and a reduced use of memory (for example, not requiring the use of buffer memories of large dimensions). Finally, modifications and variations may be made to the present solution, without thereby departing from the scope identified by the appended claims.

In particular, in a way not illustrated, appropriate filtering operations may be envisaged (for example, using low-pass filters or high-pass filters) for the pressure $S_P$ and the charge-variation $S_Q$ signals, preliminary to the processing operations described. Filtering may have the function of cleaning up the pressure and charge-variation signals $S_Q$, $S_P$ from noise or from components of disturbance at non-significant frequencies (e.g., around 50 Hz or 60 Hz for the charge-variation signal $S_Q$). It is likewise possible to carry out a frequency analysis (e.g., by means of a Fast Fourier Transform—FFT) of the charge-variation signal $S_Q$ in order to identify the features thereof in order to recognize whether the user is going upstairs or downstairs and the corresponding steps made.

In a way not illustrated, the detection device 1 can integrate further sensors (for example, a gyroscope, a temperature sensor, etc.) and envisage further processing channels dedicated to other detections.

In addition, the processing unit 6 of the detection device 1 can be configured for detecting changes in level in relation to the use of a lift by the user, on the basis of the pressure signal $S_P$ and of the corresponding pressure gradient in time, for example as described in detail in the aforesaid document U.S. Pat. No. 9,906,845 B2.

Some embodiments may take the form of or comprise computer program products. For example, according to one embodiment there is provided a computer readable medium comprising a computer program adapted to perform one or more of the methods or functions described above. The medium may be a physical storage medium, such as for example a Read Only Memory (ROM) chip, or a disk such as a Digital Versatile Disk (DVD-ROM), Compact Disk (CD-ROM), a hard disk, a memory, a network, or a portable media article to be read by an appropriate drive or via an appropriate connection, including as encoded in one or more barcodes or other related codes stored on one or more such computer-readable mediums and being readable by an appropriate reader device.

Furthermore, in some embodiments, some or all of the methods and/or functionality may be implemented or provided in other manners, such as at least partially in firmware and/or hardware, including, but not limited to, one or more application-specific integrated circuits (ASICs), digital signal processors, discrete circuitry, logic gates, standard integrated circuits, controllers (e.g., by executing appropriate instructions, and including microcontrollers and/or embedded controllers), field-programmable gate arrays (FPGAs), complex programmable logic devices (CPLDs), etc., as well as devices that employ RFID technology, and various combinations thereof.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
a pressure sensor, configured to provide a pressure signal;
an electrostatic-charge-variation sensor, configured to provide a charge-variation signal indicative of a variation of electrostatic charge; and
circuitry, coupled to the pressure sensor and to the electrostatic-charge-variation sensor and configured to detect changes in user-level based on both the pressure signal and on the charge-variation signal, wherein the circuitry is configured to:
  process a variation of the pressure signal, to detect an indication of change in user-level;
  in response to the processing of the variation of the pressure signal indicating a change in user-level, determine a context associated with the indication using the electrostatic charge-variation signal;
  determine whether the context associated with the indication is a user-step activity context; and
  in response to a determination that the context associated with the indication is a user-step activity context, determine an occurrence of a change in user-level.

2. The device according to claim 1, wherein the electrostatic-charge-variation sensor is a contact sensor configured to contact a portion of a body of a wearer of the device, and the electrostatic-charge-variation sensor, in operation, detects variations of an electrical field that occur during movement of the wearer.

3. The device according to claim 2, wherein the change in user-level is associated with the wearer going one step upstairs or one step downstairs, and the indication is detected in response to the pressure variation exceeding, in absolute value, a first pressure threshold, indicative of the variation of the pressure signal being associated with going one step up or one step down.

4. The device according to claim 3, wherein the circuitry is configured to determine the context associated with the pressure signal by extraction and analysis of features of the charge-variation signal to detect a context associated with the charge-variation signal.

5. The device according to claim 4, wherein the analysis of features of the charge-variation signal includes:
  detecting peaks of amplitude of the charge-variation signal that exceed a threshold;
  detecting patterns of the charge-variation signal; or
  combinations thereof.

6. The device according to claim 3, wherein the circuitry is configured to implement a counting of the steps up or down associated with the wearer based on the determination of an occurrence of a change in user-level.

7. The device according to claim 3, wherein the circuitry is configured to:
  set a baseline value of the pressure signal during a stationary condition; and
  at the end of the wearer climbing or descending a staircase:
    determine a difference between a current value and the baseline value of the pressure signal;
    determine a change of floor based on a comparison between the difference and a second pressure threshold, indicative of the variation of the pressure signal associated with the user going one floor up or one floor down; and
    incrementing a count of floors ascended or descended by the user based on the determining of a change of floor.

8. The device according to claim 1, wherein the device is a wearable device, and the electrostatic-charge-variation sensor comprises:
  at least one electrode configured to contact a portion of a body of a wearer of the device;
  an amplifier having an input coupled to the at least one electrode; and
  an analog-to-digital converter coupled to an output of the amplifier for supplying the charge-variation signal.

9. The device according to claim 1, comprising an integrated circuit including the circuitry, the pressure sensor, and the electrostatic-charge-variation sensor.

10. A system, comprising:
  an application processor; and
  sensing circuitry coupled to the application processor, the sensing circuitry including:
    a pressure sensor, which, in operation, generates a pressure signal;
    a charge sensor, which, in operation, generates a charge signal; and
    control circuitry, coupled to the pressure sensor and to the charge sensor, wherein the control circuitry, in operation, detects changes in user-level based on both the pressure signal and on the charge signal, wherein the control circuitry, in operation:
  detects an indication of a change in user-level based on the pressure signal;
  in response to the detecting the indication of a change in user level, determines a context associated with the indication based on the charge signal;
  determines whether the context associated with the indication is a user-step activity context; and
  in response to a determination that the context is a user-step activity context, determines an occurrence of a change in user-level.

11. The system of claim 10, wherein the charge sensor is a contact sensor, which, in operation, contacts a portion of a body of a wearer of the sensing circuitry.

12. The system of claim 11, wherein the control circuitry, in operation:
  detects the indication based on a comparison of a pressure gradient to a first pressure gradient threshold.

13. The system of claim 12 wherein the first pressure gradient threshold is indicative of a pressure gradient associated with going up or going down a stair.

14. The system of claim 11, wherein the control circuitry, in operation:
  determines the context associated with the indication based on features extracted from the charge signal indicative of a context of user-activity.

15. The system of claim 11, wherein the control circuitry, in operation:
  detects the context associated with the indication based on:
    comparisons of peaks of amplitude of the charge signal to a charge-signal threshold;
    patterns detected in the charge signal; or
    combinations thereof.

16. The system of claim 11, wherein the control circuitry, in operation, counts changes in step-level associated with the wearer based on the determined occurrences of changes in user-level.

17. The system of claim 16, wherein the control circuitry, in operation:
  sets a baseline value of the pressure signal in response to detecting a stationary condition; and
  in response to an indication the wearer has climbed or descended a staircase:
    determines a difference between a current value and the baseline value of the pressure signal;
    determines a change of floor based on a comparison between the difference and a second pressure threshold, indicative of the variation of the pressure signal associated with the wearer going one floor up or one floor down; and
    increments a count of floors ascended or descended by the wearer based on the determining of a change of floor.

18. The system of claim 10, wherein the application processor, in operation, manages context-aware operations of the system based on determined occurrences of changes in user-level.

19. A method, comprising:
  generating, using a pressure sensor of a device, a pressure signal;
  generating, using a charge sensor of the device, a charge signal; and
  detecting changes in user-level based on both the pressure signal and on the charge signal, wherein the detecting changes in user-level comprises:
  detecting an indication of a change in user-level based on the pressure signal;
  in response to detecting the indication of the change in user-level, determining a context associated with the indication based on the charge signal;
  determining whether the context associated with the indication is a user-step activity context; and
  in response to determining the context associated with the indication is a user-step activity context, determining an occurrence of a change in user-level.

20. The method of claim 19, comprising:
  placing the charge sensor in contact with a portion of a body of a user of the device.

21. The method of claim 19, comprising:
  detecting the indication based on a comparison of a pressure gradient to a first pressure gradient threshold.

22. The method of claim 21 wherein the first pressure gradient threshold is indicative of a pressure gradient associated with going up or going down a stair.

23. The method of claim 20, comprising:
determining the context based on features extracted from the charge signal.

24. The method of claim 20, comprising determining the context based on:
comparisons of peaks of amplitude of the charge signal to a charge-signal threshold;
patterns detected in the charge signal; or
combinations thereof.

25. The method of claim 20, comprising: counting changes in step-level associated with the user based on the occurrences of changes in user-level.

26. The method of claim 25, comprising:
setting a baseline value of the pressure signal in response to detecting a stationary condition; and
in response to an indication that the user has climbed or descended a staircase:
determining a difference between a current value and the baseline value of the pressure signal;
determining a change of floor based on a comparison between the difference and a second pressure threshold, indicative of the variation of the pressure signal associated with the user going one floor up or one floor down; and
incrementing a count of floors ascended or descended by the user based on the determining of a change of floor.

27. The method of claim 19, comprising:
managing context-aware operation of the device based on determined occurrences of changes in user-level.

28. A non-transitory computer-readable medium having contents that configure an electronic device to perform a method, the method comprising:
generating, using a pressure sensor of the electronic device, a pressure signal;
generating, using a charge sensor of the electronic device, a charge signal; and
detecting changes in user-level based on both the pressure signal and on the charge signal, wherein the detecting changes in user-level comprises:
detecting an indication of a change in user-level based on the pressure signal;
in response to detecting the indication of a change in user-level, determining a context associated with the indication based on the charge signal;
determining whether the context associated with the indication is a user-step activity context; and
in response to a determination that the context associated with the indication is a user-step activity context, determining an occurrence of a change in user-level.

29. The non-transitory computer-readable medium of claim 28, wherein the charge sensor is a contact sensor, and the method comprises:
placing the charge sensor in contact with a portion of a body of a user.

30. The non-transitory computer-readable medium of claim 29, wherein the method comprises:
counting changes in step-level associated with the user based on the occurrences of changes in user-level.

31. The non-transitory computer-readable medium of claim 28, wherein the contents comprise instructions executed by sensor-signal processing circuitry of the electronic device.

32. A device, comprising:
a pressure sensor configured to provide a pressure signal;
an electrostatic-charge-variation sensor configured to provide a charge-variation signal indicative of a variation over time of an electrostatic charge associated with a user body, due to transfer of charges from the user body to ground during movements of the user; and
processing circuitry, coupled to the pressure sensor and to the electrostatic-charge-variation sensor, wherein in operation, the processing circuitry:
receives the pressure signal and the charge-variation signal; and
jointly processes the pressure signal and the charge-variation signal to detect changes in level or altitude, wherein the jointly processing includes:
processing a pressure gradient over time associated with a variation of the pressure signal to detect a first indication of change in level or altitude;
processing a variation of the charge-variation signal over time to detect a second indication of change in level or altitude; and
determining the occurrence of a change in level in response to detection of the first and the second indications in a same time interval.

33. The device according to claim 32, wherein,
the change in level is associated with the user going one step upstairs or one step downstairs,
the first indication is detected in response to the pressure gradient exceeding, in absolute value, a first pressure threshold, indicative of the variation of the pressure signal associated with going one step up or one step down, and
the second indication is detected in response to detecting a variation of the charge-variation signal associated with the user going one step up or one step down.

34. The device according to claim 33, wherein the processing circuitry, in operation, detects a variation of the charge-variation signal associated with the user going one step up or down via extraction and analysis of features of the charge-variation signal.

35. The device according to claim 34, wherein the analysis of features of the charge-variation signal includes:
detecting peaks of amplitude of the charge-variation signal that exceed a fixed or adaptive threshold;
detecting specific patterns of the charge-variation signal; or
combinations thereof.

* * * * *